(12) United States Patent
Rose et al.

(10) Patent No.: US 7,651,681 B1
(45) Date of Patent: Jan. 26, 2010

(54) METHOD AND COMPOSITIONS FOR IN SITU FORMATION OF PROTECTIVE AND/OR MEDICATED FILMS ON BODY TISSUE

(75) Inventors: Seth D. Rose, Tempe, AZ (US); William H. Drummond, Newport Beach, CA (US)

(73) Assignee: Blairex Laboratories, Inc, Columbus, IN (US)

( * ) Notice: Subject to any disclaimer, the term of this patent is extended or adjusted under 35 U.S.C. 154(b) by 0 days.

(21) Appl. No.: 09/509,237

(22) PCT Filed: Oct. 19, 1998

(86) PCT No.: PCT/US98/22022

§ 371 (c)(1), (2), (4) Date: Mar. 28, 2000

(87) PCT Pub. No.: WO00/23022

PCT Pub. Date: Apr. 27, 2000

(51) Int. Cl.
*A61K 31/74* (2006.01)
*A61K 9/70* (2006.01)

(52) U.S. Cl. .................................. 424/78.08; 424/443
(58) Field of Classification Search .............. 424/70.03, 424/59, 422, 484, 78.08, 81, 443, 447
See application file for complete search history.

(56) References Cited

U.S. PATENT DOCUMENTS

| | | | |
|---|---|---|---|
| 4,244,948 A | | 1/1981 | Boghosian et al. |
| 4,247,547 A | * | 1/1981 | Marks ........................ 424/240 |
| 4,374,126 A | | 2/1983 | Cardarelli et al. |
| 4,381,296 A | | 4/1983 | Tinnell |
| 4,434,181 A | | 2/1984 | Marks et al. |
| 4,533,540 A | * | 8/1985 | Blank .......................... 424/28 |
| 4,826,677 A | * | 5/1989 | Mueller et al. ................. 424/78 |
| 4,913,897 A | | 4/1990 | Chvapil |
| 5,013,769 A | | 5/1991 | Murray |
| 5,080,889 A | * | 1/1992 | Katada et al. ................. 424/63 |
| 5,081,158 A | * | 1/1992 | Pomerantz .................. 514/781 |
| 5,547,662 A | | 8/1996 | Khan et al. |
| 5,849,280 A | * | 12/1998 | Rechelbacher et al. ... 424/70.11 |
| 5,874,072 A | * | 2/1999 | Alwattari et al. ........... 424/70.7 |
| 5,955,097 A | | 9/1999 | Tapolsky et al. ............. 424/434 |

FOREIGN PATENT DOCUMENTS

EP  801 077  10/1997

OTHER PUBLICATIONS

Stoughton, Archives of Dermatology, 1962, vol. 86, pp. 608-610.
Stoughton, Archives of Dermatology, 1985, vol. 121, pp. 63-67.
Landol, Journal of Polymer Science: Polymer Chemistry Edition 20, pp. 443-466 (Wiley, 1982).
Russell, Rodu B. "Performance of a hydroxypropyl cellulose film former in normal and ulcerated oral mucosa" *Oral Surg. Med. Oral Pathol*, Jun. 1988; 65(6) 699-703.
Zerwekh, Kitano T et al., "Viscous carboxymethylcellulose in the prevention of epidural scar formation" *Spine*, Jul. 1991; 16(7): 820-823.
Robinson, Park H., "Mechanisms of mucoadhesion of poly (acrylic acid) hydrogels" *Pharm. Res* Dec. 1981; 4(6): 457-464.
Soltesz, Wang X et al., "Water-soluble ethylhydroxyethyl cellulose: a new agent against bacterial translocation from the gut after major liver resection", *Scand J. Gastroenterol*, Sep. 1994; 29(9): 833-840.
Gates, KA, et al., A new bioerodible polymer insert for the controlled release of metronidazole:*Pharm Res*, 1994 No; 11(11): 1605-1609.
Tamburic S, Craig, The effects of ageing on the rheological, dielectric and mucoadhesive properties of poly (acrylic acid) gel systems'*Pharm Res*Feb. 1996; 13(2): 279-283.
Sahlin, JJ, Peppas, Enhanced hydrogel adhesion by polymer interdiffusion: use of linear poly (ethylene glycol) as an adhesion promoter'*J, Biomater Sci Polym Ed* 1997; 8(6): 421-436.

\* cited by examiner

*Primary Examiner*—Blessing M Fubara
(74) *Attorney, Agent, or Firm*—E. Victor Indiano; Indiano Vaughan LLP

(57) ABSTRACT

Methods and compositions for forming protective and/or medicated films on body tissue. Liquid compositions contain a hydrophobically modified polymer, other than an esterified lower-hydroxyalkyl-substituted cellulose, suspended or dissolved in a solvent. The modified polymer is soluble in the solvent but insoluble in body fluids. The compositions may optionally contain a separate medicinal component, i.e., one which is present in addition to any medications, if any, present in the solvent, in the modified polymer and in any other additive components such as flavors, skin penetrants, preservatives, other solvents for the additives, etc. A protective and/or medicated film is formed in situ upon body tissue by applying the liquid composition to the tissue and separating the solvent from the composition, e.g., by vaporization.

1 Claim, No Drawings

METHOD AND COMPOSITIONS FOR IN SITU FORMATION OF PROTECTIVE AND/OR MEDICATED FILMS ON BODY TISSUE

This application is a 371 of PCT/US98/22022, filed Oct. 19, 1998.

This invention relates to methods for in situ formation of protective films on body tissue.

In addition, the invention relates to compositions that form medicated films in situ on body tissue.

In another respect, the invention concerns methods and compositions for in situ formation of protective and/or medicated films on body tissue.

According to another aspect, the invention provides methods and compositions for in situ formation of films on body tissue, films that provide slow or sustained release of topical medicaments and/or provide a protective coating for the underlying tissue.

Pharmacologists have long sought to provide methods and compositions for in situ formation of protective and/or medicated films on body tissues, such that a protective film could be formed and maintained at specific locations on or inside a human or animal body. The underlying body tissue may have a cut, abrasion, wound or lesion, or may be infected. Such a protective film could prevent insult of the underlying wound or lesion by external substances, germs, etc. or prevent infection of surrounding healthy tissue by preventing spread of the infection, e.g., by viral shedding. Alternatively, the body tissue, to which a medicated film is applied, may be healthy, but there it is desired to administer a drug for absorption through the skin or the surface of an internal organ. In particular, medications, such as topical anesthetics, corticosteroids, bactericidal and viricidal sterilization agents and the like are difficult to maintain in proper contact with various body tissues, because of physical movement of the underlying or adjacent tissues or abrasion of such tissues by the movement of wound dressings, clothing, etc. It is especially difficult to maintain protective and/or medicated films on wet or moist tissues, such as mucosal tissues, and upon other body tissues which exude or secrete blood, perspiration, or other aqueous body fluids.

In the case of mucosal tissue, it is considered practically impossible to reliably maintain a protective or medicinal treatment composition at the treatment site. The mucosal tissues are glabrous and initially wet which interferes with such compositions at their intended locations.

The use of topical anesthetics for reducing pain is known. For example, commercially-available preparations containing benzocaine or corticosteroids and various thickeners are widely used. However, these do not form coherent, persistent films in the mouth and are easily displaced from the ulcer site by saliva and physical movement of the surrounding tissues.

An intra-oral ointment base for use in the oral cavity has been provided which consists essentially of sodium carboxymethylcellulose and pectin. However, such ointments are not considered sufficiently persistent to solve the basic problem of forming a protective film over an oral lesion and/or maintaining a topical analgesic or other medication in contact with an ulcer for up to several hours.

Topical adhesive dosages for mucosal ulcers or lesions have also been proposed in the form of a two-phase tablet having a pre-formed adhesive peripheral film of hydroxypropylcellulose (hereafter "HPC") with a medication carried in an oleaginous core of cocoa butter which is next to the underlying tissue. This device was reported to adhere to the mucosa of dogs for thirty minutes to six hours.

Mixtures of HPC and polyvinyl acetate have been proposed as film-forming carriers for medications, but, according to our knowledge, no use of such systems for intra-oral application of topical medicines has resulted.

Precast films of HPC carrying analgesics and antibiotics has been reported anecdotally for the treatment of pain of leukoplakia.

Alkylcellulose and/or cellulose ether compounds have been used as thickeners or ointment bases for a wide variety of medicaments. For example, hydroxyethylcellulose (hereafter, "HEC") and/or HPC was used to form a gel for application of the topical acne medications of U.S. Pat. No. 4,244,948 to Boghosian, et al. HEC was used to form a water soluble lotion or gel in a cold sore/fever blister medication sold as "Kank-A®", a registered trademark of Blistex, Inc. A water-soluble film formed of HPC was used as the carrier for a bactericide, in a bovine teat-dip composition in U.S. Pat. No. 4,434,181 to Marks, et al.

Heretofore, it was known that the pain associated with cold sores, fever blisters and recurrent aphthous stomatitis (RAS) lesions, was temporarily alleviated by the medicinal composition of the Tinnell U.S. Pat. No. 4,381,296, in an alcohol-esterified HPC-water carrier. However, clinical tests did not show that the pain reduction was due to the action of the medications, but that the principal analgesic effect was believed to be due to a formation of a protective film which formed over the lesions. This film, which persisted on the lesion for several hours, acted as a barrier to insults by air, foods, saliva, etc. This composition was first sold by Zila Pharmaceuticals, Inc. in the early 1980s under the trademark "HERPAWAY" and later sold, until 1993, under the trademark "ZILACTIN"®.

Later, in the mid-1980s, it was discovered that the film forming ability of HERPAWAY and ZILACTIN® compositions was due to partial esterification of the HPC component by the medicinal components of Tinnell '296, rather than by simple deposition of unmodified HPC material per se upon the lesion, upon vaporization of the alcoholic solvent.

Later, a gel-like product has been marketed which is believed to contain hydroxyethylcellulose (HEC) salicylic acid, ethyl alcohol and benzocaine. The composition does form a film on body tissue, but there are indications that it causes irritation of the underlying tissue. It is not known if the salicyloyl ester of HEC is present or is formed in this composition.

It was also known (Stoughton, *Arch. Dermatol.* 1962, 86, 608-610; Stoughton, *Arch. Dermatol.* 1985, 121, 63-67) to potentiate the effects of topical medications by first applying a quantity of the medicament to body tissue (epidermis), usually in a lotion or gel carrier, and then covering the medicament-treated site with a pre-formed impermeable elastic film or membrane. The membrane maintained the medicament in contact with the tissue to which it was applied and prevented physical dislocation of the medication by body fluids, e.g., by washing the medication away during normal bathing, dislocation by movement of the underlying tissue and/or by dislocation by abrasion of the medicament by clothing or contact of the other body tissues or objects.

Until our invention, there was only one known composition which would provide the same medication-potentiating results as those described by Stoughton, but which achieved that result by direct in situ formation of a medicated film on body tissue by applying a liquid composition containing the drug. This composition was described by Pomerantz in U.S. Pat. Nos. 5,081,158 and 5,081,157. The composition was a liquid (gel) comprising partially-esterified HPC in a volatile solvent (the original HERPAWAY/ZILACTIN), plus a separate medicinal component, i.e., separate and in addition to any other medicaments, if any, which might have been dispensed from the original HERPAWAY/ZILACTIN compositions. Upon application of these compositions to body tissue and "drying" of the liquid (gel) composition (by volatilization of the solvent), these compositions formed an adherent, coherent in situ-deposited medicated film containing the separate medication on the body tissue, even on wet mucosal tissue, and effectively dispensed the separate medication to the underlying body tissue.

Accordingly, later versions of the original ZILACTIN® product, sold since 1993-94, contained separate medicinal components, namely benzocaine (ZILACTIN®-B) and benzyl alcohol (ZILACTIN®), components which are recognized as effective for the treatment of cold sores and fever blisters.

Subsequent unpublished research has confirmed that the original ZILACTIN® films included very small quantities of HPC esterified by salicylic and/or tannic acid components. This conclusion was supported by published literature, authored by Landoll, confirming that normally water-soluble HPC is rendered insoluble in water, if modified by attachment of very small quantities (as low as 0.9-1.3 wt %) of hydrophobic groups (long-chain hydrocarbons), through ether-linkages, to the HPC backbone. The insoluble hydrophobe-modified polymer, is however, soluble in aqueous ethanol. J. Polym. Sci., Polymer Chemistry Ed., 20, 443-455 (Wiley, 1982).

Well prior to the publication of the Landoll paper, it was known that hydrophobic groups impart water-insolubility to chemical substances, whereas hydrophilic groups impart water-solubility. In particular, the water-solubility of polymers is strongly dependent on the hydrophilicity and hydrophobicity of the repeating units of the polymer. For example, it is known from the prior art that the copolymer poly(vinyl acetate-co-vinyl alcohol) contains both a hydrophilic substituent (hydroxyl group) and a hydrophobic substituent (the methyl group of acetate), and at greater than 30 mole % of the methyl-group-containing monomer, the copolymer is insoluble in water. It was also known from the Landoll paper, that hydrophobic modification of hydrophilic (i.e., water-soluble) polymers such as HPC renders the modified polymer water insoluble at body temperatures, even at low levels of introduction of the hydrophobic modifier. For example, the introduction of only approximately three hydrophobic groups (e.g., $C_{12}$) per polymer chain of HPC (MW 50,000) renders the modified polymer insoluble in water. Theoretical explanations of this phenomenon envisage the formation of three-dimensional networks of polymer molecules formed by the hydrophobic bonding, or "association", of the limited number of hydrophobic groups attached to the polymer chains. These "liaisons" between molecules serve to greatly increase the effective molecular weight of the polymer, dramatically reducing its solubility. Increased viscosity is also observed for aqueous solutions of less extensively modified polymer.

We have now discovered that the principle of hydrophobic modification of polymers is effectively employed to produce new liquid compositions for forming films in situ upon body tissues. These compositions are formed from a polymer and an agent ("interaction agent") that interacts with the polymer to form a product ("interaction product") which is substantially insoluble at normal body temperatures in water or aqueous body fluids, but which is soluble in a nontoxic volatile solvent. Application of this interaction product, dissolved in a non-toxic volatile solvent, will result in the in situ formation of a film of the interaction product on body tissue, including moist surfaces such as mucosal tissues, upon evaporation of the volatile solvent, and the film is persistent because it is substantially insoluble in aqueous-based body fluids. Depending on the chemistry of the specific method used to prepare the interaction product, it can either be prepared separately and then dissolved in a suitable volatile solvent, or, alternatively, if the reactants used to prepare the interaction product, and reaction byproducts, are pharmacologically acceptable, the interaction product can be prepared in situ in our liquid compositions. The interaction between the polymer and the interaction agent can occur during manufacture or storage of the liquid compositions, during application of the liquid compositions to body tissues, or even during "drying" of the liquid compositions by vaporization of the volatile solvent or during only some or all such times.

Furthermore, because substantially the same result is obtained by copolymerization of monomers with hydrophilic and hydrophobic groups, those copolymer compositions and methods of preparation are included as specific embodiments of the general principles of this invention. In this case the agent which interacts (copolymerizes) with the polymer to form the water-insoluble interaction product is itself another polymer, copolymer, modified polymer or modified copolymer.

Briefly, then, in accordance with our invention, we provide a method of forming a film in situ on body tissue. Our method comprises the steps of (a) applying to body tissue a liquid composition which includes a non-toxic volatile solvent and a solubility-modified polymer, other than an esterified HPC (of the Pomerantz patents), or a copolymer, which is soluble in the solvent, but insoluble in body fluids; and (b) separating the solvent from the liquid composition, to form a persistent film. The film can act merely as a protective "bandage" film which excludes air, body fluids and other foreign materials from an underlying lesion, or which prevents the escape of substances, e.g., viruses, from a lesion underlying the film, which may cause spread of an infection to or irritation of surrounding healthy tissue. These liquid compositions of the invention may also contain additional medicinal components (i.e., in addition to those components, if any, of the film-forming compositions which may have an incidental medicinal effect) which are effectively dispensed from these liquid compositions and/or from the in-situ-deposited films formed therefrom.

As will be apparent to those skilled in the art the liquid compositions of the invention may also include additive components for modifying the characteristics of the liquid compositions and/or for facilitating the manufacture of the compositions, including, without limiting the generality thereof, flavors, plasticizers, dermal penetrants, preservatives, as well as other "secondary" solvents which are used to dissolve the interaction agent(s) and other additive components. If any of these additive components have any incidental medicinal effects, it is intended that the term "separate medicinal component means a medicinal component in addition to those present in the primary solvent, in the modified polymer or copolymer and in the additive components.

The method of the invention also contemplates the steps of (a) forming an interaction product by interaction of a polymer (which may include HPC) and at least one interaction agent, other than an esterification agent (as in the Pomerantz '158 patent), which interacts with the polymer (and possibly with other components of the interaction mixture), to form an interaction product. The interaction agent is soluble in a solvent, but insoluble in body fluids; (b) solubilizing the interaction product in the solvent; and (c) forming a film in situ on body tissue by applying the solvent solution of the interaction product to body tissue and (d) separating the solvent from the liquid composition. As previously disclosed, the interaction product can be separately manufactured and then solubilized in the solvent or, alternatively, the interaction product can be formed in situ, during manufacture and/or storage of the liquid composition or during the application-drying of the liquid composition upon body tissue, or both.

Our invention also contemplates a liquid composition which forms a medicated film in situ upon body tissue, comprising: (a) a solvent; (b) an interaction product formed by interaction between a polymer and an agent other than an esterification agent, which interaction product is soluble in the solvent, but insoluble in body fluids; and (c) a medicinal component, in addition to any other medicament, if any, in the polymer, the interaction agent(s), the interaction product, and any other functional additives in the composition. Also the invention contemplates such a liquid composition, containing such a separate medicament, but in which the substrate polymer is a polymer other than a lower hydroxyalkyl-substituted cellulose, in which case, the interaction agent can include esterification agents.

The solvent for the interaction product is preferably a volatile solvent, such as, for example volatile polar solvents. As used herein, the term "volatile" solvent means a solvent which evaporates (vaporizes) from the liquid compositions, after they are applied to the body tissue, at a rate which is sufficient to cause formation of the film on the body tissue within a practical length of time, e.g., 30 seconds-5 minutes. This permits application of liquid compositions by persons with limited medical skills, e.g., technicians or even the patients themselves. The application site can be substantially immobilized, and abrasion of the site by other body parts, clothing, etc., and irrigation by body fluids can normally be suspended or eliminated during this suitable short period of time, to permit formation of the film. After the film forms on the tissue, the film is sufficiently adherent and coherent, such that it is persistent at the application site for a time sufficient to permit the film to perform its intended function, i.e., to temporarily relieve pain, by forming a physical barrier over the application site, and/or to permit the film to hold a separate medication against the tissue (lesion, wound, etc.), for a sufficient period of time to achieve practical therapeutic effects, e.g., from 15-30 minutes to as high as upwards of 4-6 hours.

The particular solvent for forming the liquid composition is selected for its ability to dissolve the components of the liquid composition, the ability to maintain the interaction product in solution or suspension until application of the composition to the treatment site and the ability to be rapidly separated from the composition after application to the body tissue, e.g., by vaporization, extraction, etc. as well as for its non-toxic characteristics when the composition is applied in the amount and for the time necessary to form a protective and/or medicated film. Obviously, the solvent should not be toxic to the body in the quantities and contact times employed and it must be chemically compatible with the other components of the liquid compositions, i.e., these solvents are those which are "pharmacologically acceptable". Suitable solvents will be readily identified by those skilled in the art having a regard for the disclosures herein, e.g., volatile polar solvents which are medically compatible with body tissue and which are chemically compatible with the other components of the liquid compositions, i.e., such solvents which are "pharmacologically acceptable". Advantageously, the solvent is a lower alkyl alcohol, e.g., preferably ethyl alcohol or isopropyl alcohol. Ethyl alcohol is preferred when the film is to be deposited in the oral cavity, whereas isopropyl alcohol is suitable for use in depositing films on the skin.

The term "liquid" composition includes liquids, the viscosity of which ranges from that of a "runny" liquid, to a viscous lotion or even to a spreadable self-supporting gel. Advantageously, in order to permit more accurate application of liquid to a specific treatment site, e.g., a fever blister or cold sore or small wound, the liquid composition is preferably in the form of a spreadable gel which can be conveniently filled into flexible dispensing tubes which can be squeezed to dispense the gel directly onto the application site or onto an applicator, such as the tip of a finger or a swab, from which it is applied to the body tissue.

The term "soluble" (in the solvent) means that the components of the liquid composition are either completely dissolved in or at least substantially uniformly dissolved or suspended or substantially uniformly dispersed in the liquid composition, such that the liquid composition is sufficiently stable to withstand separation of one or more of its components until the liquid composition can be applied to the body tissue. This may vary from a period of time of only a few minutes (in the case of the liquid compositions which are to be applied soon after formulation), to up to several years (for products sold through normal ethical or over-the counter channels). Extended shelf-life can be determined by accelerated aging tests which are well known and accepted in the art.

The term "insoluble" in body fluids means that the interaction product is sufficiently resistant to solubilization or other film-destructive actions of body fluids, e.g., saliva, perspiration, blood, and the like, to enable the in situ deposited film to remain adherent to the body tissue and sufficiently coherent to allow the film to perform its intended function, i.e., to act as a physical protective coating for the underlying tissue, and/or to dispense the separate medication therefrom.

The term "non-toxic" means that a component is not injurious to body tissues or body functions at the concentrations employed and/or for the time that the component is in contact with the tissue.

The term "separating" the solvent from the liquid composition means the removal of the solvent from the liquid composition, after application to body tissue, by any suitable technique, such that the interaction product is deposited as a coherent, adherent film on the tissue, for example, by simply air-drying the applied liquid composition, by accelerated air-drying (as by heating the applied liquid composition with hot air or a heat lamp) or by preferentially extracting the solvent from the liquid composition by gently irrigating the application site with an aqueous solvent which dissolves part or all of the volatile solvent and simultaneously assists in precipitating the water-insoluble interaction product and/or separate medication, as a coherent, persistent film.

The terms forming a film "in situ" or film-forming "in situ" (upon body tissue) means that the film autogeneously forms on the body tissue upon separation of the solvent component of the liquid compositions, as distinguished from films which are pre-formed, e.g., by casting, extrusion or compression or thermal molding, and thereafter applied to the body tissue.

The term "upon" body tissue does not exclude the possibility that an intermediate film of another chemical or physical nature may lie between at least parts of the interaction product film and the body tissue. For example, the application of a liquid composition containing ethyl alcohol as the solvent to moist mucosal tissue causes more or less immediate denaturation of saliva and/or tissue proteins which underlie the in situ deposited film described herein. Such an intermediate denatured-protein film does not appear to degrade the effectiveness of the interaction product film, either as a protective barrier or as carrier for a separate medication. In fact, such an intermediate layer or material appears to actually assist in adhesion of the in situ-deposited interaction product film to the underlying tissue.

According to the presently preferred embodiments of the invention, the interaction product component of the compositions of the invention is present in the composition in an amount of from about 1-10% by weight of the final composition. The proportion of the interaction product in the composition affects the time required for the composition to air dry and form a tough adhesive film. At lower contents of the interaction product, the compositions dry more slowly, but the resultant film is more coherent and abrasion-resistant. At higher contents, the film forms more quickly by air drying, but the resultant film is less coherent and adhesive owing to the fact that the portion of the film at the surface of the applied composition and at the body tissue surface dry at different rates.

At present, we prefer to employ enough of the interaction product and solvent in the final composition to yield an easily-applied gel which dries to form the in situ-deposited film in a practical length of time, as distinct from a runny liquid or lotion which is difficult to maintain on the intended treatment site for a time sufficient to form the in situ-deposited film and which may take too long to form the film. Likewise, the amount of the interaction product should not be so great or the amount of solvent so small as to form a stiff gel, which may be difficult to dispense or to spread on the application site. This optimum quantity may vary depending on the exact chemical composition of the interaction product and the nature of the other components of the final compositions. This optimum quantity can, however, be readily determined by persons skilled in the art, without undue experimentation, having regard for this disclosure.

The invention can be visualized as using an interaction product, comprising a three-part molecule composed of a polymer, a "linker", and a hydrophobic group, schematically represented as:

(polymer)-(linker)-(hydrophobic group)

wherein the linker may or may not contain atoms that were originally part of the polymer and/or the hydrophobic group. These major constituents of the interaction product molecule consist of:

(1) a polymer, including synthetic polymers, natural polymers, and synthetically modified natural polymers, including homopolymers, as well as block, alternating, and random copolymers.

(2) a "linker" that may consist of organic functional groups that are known to join differing domains of complex organic molecules, including but not limited to esters (O=C—O) and their sulfur derivatives [i.e., thio (S=C—O), thiolo (O=C—S), and dithio (S=C—S) derivatives], ethers (—O—) and their thio derivatives (—S—), urethanes [O—(C=O)—N] and their thio derivatives (e.g., xanthates), carbonates [O—(C=O)—O] and their thio derivatives, amides (O=C—N) and imides and their thio derivatives, ureas [N—(C=O)—N] and their thio derivatives, amines (C—N), imines (C=N), acetals and hemiacetals [RCH(OR')(OR") and RCH(OR')(OH)] and their thio derivatives, ketals and hemiketals [RR'C(OR")(OR''') and RR'C(OR")(OH)] and their thio derivatives, sulfonates [—S(=O)₂—O], sulfinates [—S(=O)—O], sulfonamides [—S(=O)₂—N], sulfinamides [—S(=O)—N], disulfides (—S—S—) and their various mono- and polyoxides, sulfoxides [R—S(=O)—R'], sulfones [R—S(=O)₂—R'], carbon-carbon single or multiple bonds, alcohols [RC(OH)R'], ketones [R—(C=O)—R'] and thioketones [R—(C=S)—R'], phosphate esters [RO—P(=O)(O⁻)—OR' and RO—P(=O)(OR')(OR")], phosphamides [RO—P(=O)(O—)—NR' and RO—P(=O)(OR')(NR") and RO—P(=O)(NR')(NR") and O=P(NR)(NR')(NR") and their less substituted analogues, e.g., RO—P(=O)(NR')(NH₂)], phosphonate esters [R—P(=O)(O⁻)—OR'], and phosphonamides [R—P(=O)(O⁻)—NR' and R—P(=O—)(NR')NR" and their less substituted derivatives], phosphinate esters [R—P(=O)—OR'], phosphinamides [R—P(=O)—NR'], or combinations thereof, wherein, the various R, R', R", and R''' groups are the polymer and/or hydrophobic groups being linked.

(3) a hydrophobic group that may principally derive its hydrophobicity from a hydrocarbon group, including saturated and unsaturated hydrocarbon chains (e.g., terpenes) and rings (i.e., cycloalkyl) and combinations thereof (e.g., steroids), which may contain one or more heteroatoms in the chains and/or rings, or fats, oils, waxes, or from a haloalkyl group, such as a partially or entirely fluoro-substituted alkyl chain [e.g., (CF₂)ₙ(CF₃)] or ring or combination thereof, such groups typically exhibiting greater hydrophobicity than the comparable-length parent unsubstituted hydrocarbon, or from an aromatic or aralkyl group (i.e., combined aromatic and aliphatic constituents), or heterocyclic groups (e.g., furyl, thienyl), or from a silicone (e.g., dimethylsiloxane unit or units) or to other heteroatom-containing hydrophobic group, and including any other group with generally recognized hydrophobic character.

Specific embodiments of the invention, which are chosen to illustrate the practice of the invention and which are not intended as limitations on the scope thereof, include:

(1) HPC(HPC—OH), a synthetically modified natural polymer, hydrophobically modified by covalent attachment of a long hydrocarbon chain-via a urethane linkage to a hydroxyl group of the HPC, as for instance through the reaction of HPC—OH with octadecyl isocyanate, shown below:

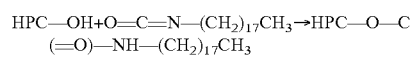

(2) Carboxymethylcellulose, a synthetically modified natural polymer, hydrophobically modified by covalent attachment of a hydrocarbon chain via an amide linkage, for instance through the reaction of the carboxymethylcellulose with a condensing agent and N-hydroxysuccinimide to produce an active ester [CMC—C(=O)—X], followed by treatment with a long-chain amine (e.g., octadecylamine), shown below:

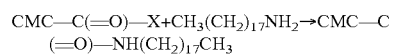

(3) Poly(vinyl alcohol-co-vinyl acetate), a synthetic vinyl polymer, hydrophobically modified by covalent attachment of a hydrocarbon chain via an ester linkage, as for instance through the reaction of the polymer with a fatty acid chloride in the presence of a base, shown below (in which block, random, or alternating copolymer is not meant to be implied by the structural representation):

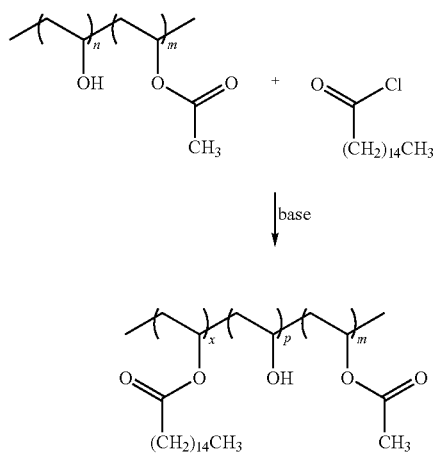

(4) Polyiminodiacetamide, a synthetic polyether, hydrophobically modified by covalent attachment of a perfluoroalkyl chain via a sulfonamide linkage, as for instance through the reaction of the polymer-bound amine functional groups with perfluoro-1-octanesulfonyl fluoride, shown below:

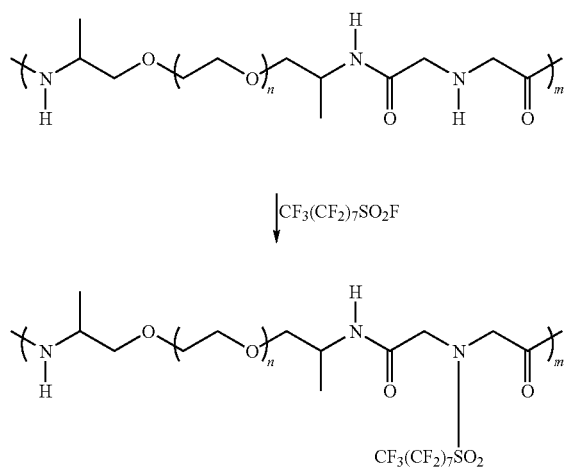

Preparation of the Hydrophobically Modified Polymers described above may be carried out in homogeneous solution by use of a suitable solvent or by emulsion techniques, in which a polymer-containing phase is mixed with the hydrophobic reactant-containing phase for linkage formation in the two-phase mixture.

The following specific examples are presented to illustrate the preparation of compositions which are useful in accordance with various embodiments of the invention. They are not intended to indicate or limit the scope of the invention, which is set forth only in the appended claims.

EXAMPLE 1

Synthesis of Hydrophobically Modified HPC

A urethane linkage is employed in the hydrophobically modified polymer described in this example.

To a solution of 5.0 g of HPC (molecular weight 50,000 and molar substitution 3.0) in 575 mL of tetrahydrofuran (or an appropriate volume of another suitably unreactive solvent, such as dioxane or pyridine) under an inert atmosphere, is slowly added with stirring a solution of octadecyl isocyanate in 50 mL of the same solvent. To achieve approximately 1% bound modifier, the amount of octadecyl isocyanate should be 0.05 g in excess of the amount destroyed by any moisture contained in the HPC. After a 1-day reaction time, the reaction mixture is cautiously poured into cold water to quench the reaction and precipitate the product. The product is collected by filtration or centrifugation, washed with water, and air dried. The degree of substitution is determined by nitrogen analysis. Variation of the amount of modifier bound, if required to optimize the water solubility of the interaction product, can be achieved by variation of the reaction time, temperature, and/or ratio of the reactants.

EXAMPLE 2

Synthesis of Hydrophobically Modified Carboxymethylcellulose

An amide linkage is employed in the hydrophobically modified polymer described in this example.

To a suspension of 5 g of carboxymethylcellulose in 25 mL of dioxane containing 0.1 g of N-hydroxysuccinimide is added 3 g of 1,3-dicyclohexylcarbodiimide. The reaction mixture is stirred for 4 hours to allow formation of the active ester of the polymer-bound carboxyl groups. The polymer is collected by filtration, washed with dioxane, and transferred to a solution of 0.05 g of octadecylamine in 25 mL of dioxane, to achieve approximately 1% bound modifier. After a 1-day reaction time, the reaction mixture is poured into aqueous acid to quench the reaction, solubilize any remaining amine, and precipitate the product. The product is collected by centrifugation, washed with water, and air dried. The degree of substitution is determined by nitrogen analysis. To optimize the water solubility of the modified polymer, some variation of the amount of modifier bound may be required, which can be achieved by variation of the reaction time, temperature, and/or the ratio of the reactants.

EXAMPLE 3

Synthesis of Hydrophobically Modified Poly(Vinyl Alcohol-Co-Vinyl Acetate)

An ester linkage is employed in the hydrophobically modified polymer described in this example.

To 5 g of poly(vinyl alcohol-co-vinyl acetate) whose vinyl acetate content is less than 30 mole %, prepared by the controlled saponification of poly(vinyl acetate), is added 50 mL of pyridine, and the mixture is stirred overnight. To this stirred mixture is added 0.057 g of palmitoyl chloride dissolved in 5 mL of pyridine, to achieve approximately 1% bound modifier. After a reaction time of 1 day, the mixture is added to aqueous hydrochloric acid to precipitate the product. The product is collected by filtration, washed with water, and redissolved in ethyl alcohol and reprecipitated with water, for purification, and air dried. The degree of substitution is determined by saponification and fatty acid analysis. For optimal modified polymer solubility, variation of the amount of modifier bound can be achieved by variation of the reaction time, temperature, and/or ratio of the reactants.

EXAMPLE 4

Synthesis of Hydrophobically Modified Polyiminodiacetamide

A sulfonamide linkage is employed in the hydrophobically modified polymer described in this example. To a solution of 5 g of polyiminodiacetamide in 25 mL of toluene is added 0.05 g of perfluoro-1-octanesulfonyl fluoride dissolved in 5 mL of toluene, to achieve approximately 1% bound modifier. After a reaction time of 1 day, the mixture is cautiously added to cold water to quench the reaction and precipitate the product. Finely divided silicic acid may advantageously be added as catalyst. After 2 hours at 60 deg C., the reaction mixture is cooled, and the product is collected by filtration, washed with water, and air dried. The degree of substitution is determined by fluorine and sulfur analyses. For optimal modified polymer water-solubility properties, variation of the amount of modifier bound is achieved by variation of the reaction time, temperature, and/or ratio of the reactants.

EXAMPLE 5

Synthesis of Hydrophobically Modified Hydroxyethylcellulose (HEC)

An ester linkage is employed in the hydrophobically modified polymer in this example.

To 5 g of HEC in 50 mL of pyridine is added 0.057 g of palmitoyl chloride dissolved in 5 mL of pyridine, to achieve approximately 1% bound modifier. After a reaction time of 1 day, the mixture is added to aqueous hydrochloric acid to precipitate the product. The product is collected by centrifugation, washed with water, and redissolved in isopropyl alcohol and reprecipitated with water, for purification, and air dried. The degree of substitution is determined by saponification and fatty acid analysis. For optimal modified polymer water-solubility properties, variation of the amount of modifier bound can be achieved by variation of the reaction time, temperature, and/or ratio of the reactants.

EXAMPLE 6

Preparation of Hydrophobically Modified HEC, During Manufacture/Storage of a Film-Forming Composition In this example hydrophobically modified HEC via an ester linkage is prepared during the manufacture/storage of the final film-forming composition.

To 1 g of HEC in 5 g of polyethylene glycol is added 0.035 g of octadecenylsuccinic anhydride and 0.015 g of triethanolamine.

After a reaction time of 1 day, to the mixture is added 13.95 g of aqueous ethanol to destroy any unreacted anhydride and to dissolve the modified HEC. For adjustment of the degree of substitution to obtain optimal film water-solubility properties, the amount of HEC, the anhydride, triethanolamine, and polyethylene glycol, as well as reaction time, reaction temperature, and pH can be varied.

10 wt. % benzocaine is added to the dissolved modified HEC. The resultant composition is shelf-stable and functions effectively to treat the pain of cold sores, fever blisters and RAS lesions, by a combination of the protective "bandage" film formed in situ after application of the composition to the site of lesions and the anaesthetic effect of the benzocaine. The film remains in place on the lesion for several hours.

EXAMPLE 7

Other Film-Forming Compositions Containing a Separate Medication

Therapeutically effective quantities of various topical medicines are incorporated into ethanol solutions containing 2-8 wt % of the modified polymers of Examples 1-6. The resulting mixtures are shelf-stable and are topically applied to body tissue and air-dried, forming coherent, adherent films containing the medicines. The medicine migrates to the treatment site to effectively accomplish the desired therapeutic result.

Anesthetics

Benzocaine

Dyclonine hydrochloride

Hexylcaine hydrochloride

Pramoxine hydrochloride

Butamben picrate

Tetracaine hydroiodide

Anti-Inflammatory Agents

Hydrocortisone acetate

Betamethasone valerate

Triamcinolone acetonide

Fluocinonide

Dexamethasone

Methylprednisone acetate

Antibiotics

Clindamycin

Erythromycin

Meclocycline sulfosalicylate

Tetracycline

Chlorhexidine

Neomycin

Polymyxin B sulfate

Bacitracin

Sulfadoxine

Antifungal Agents

Clotrimazole

Miconazole

Nystatin

Acyclovir

Interferon

Vidarabine

Betadine

Miscellaneous Topical Agents

Salicylic acid

Isotretinoin

Aloe Vera

Alclomethasone dipropionate

Caprylic acid

Lindane

Having described the invention in such terms as to enable one skilled in the art to understand and practice it and, having identified the presently preferred best modes of the invention, we claim:

1. The method of forming a film in situ upon a mucosal tissue that is wet or moist, comprising:
    providing a liquid composition comprising,
    1) a volatile solvent; and
    2) a water soluble polymer selected from the group consisting of carboxymethylcellulose, and hydroxyethyl cellulose, the water soluble polymer being capable of attaching to a hydrophobic group through covalent bonding;
    3) a compound selected from the group consisting of octadecyl isocyanate, hydroxysuccinimide, perfluoro-1-octanesulfonyl fluoride, palmitoyl chloride, and fatty acid chloride; wherein preparation and use of the liquid composition includes steps of modifying the water solubility of the polymer in the liquid composition by attaching a hydrophobic group of the compound selected from the group consisting of octadecyl isocyanate, hydroxysuccinimide, perfluoro-1-octanesulfonyl fluoride, palmitoyl chloride, and fatty acid chloride to the water soluble polymer to produce a water insoluble interaction product;

applying the liquid composition to a mucosal tissue that is wet or moist;

evaporating the solvent from the liquid composition in situ; and forming a film which adheres to a mucosal tissue that is wet or moist.

\* \* \* \* \*